United States Patent [19]

Westerman

[11] Patent Number: 4,576,184

[45] Date of Patent: Mar. 18, 1986

[54] DRUG ABUSE DETECTION

[75] Inventor: S. Thomas Westerman, Shrewsbury, N.J.

[73] Assignee: Pharmometrics Corporation, New Brunswick, N.J.

[21] Appl. No.: 603,243

[22] Filed: Apr. 23, 1984

Related U.S. Application Data

[63] Continuation of Ser. No. 297,997, Aug. 31, 1981, abandoned.

[51] Int. Cl.[4] .............................................. A61B 5/04
[52] U.S. Cl. .................................................... 128/733
[58] Field of Search ......................................... 128/733

[56] References Cited

U.S. PATENT DOCUMENTS 3,000,271  9/1961  Harvey ................................. 128/733
3,774,593  11/1973  Hakata et al. ....................... 128/733

OTHER PUBLICATIONS

Jongkees et al., "Acta Physiology-Pharmacology NeerLandica", vol. 9, 1960, pp. 240-241, 272-275.

Primary Examiner—William E. Kamm
Attorney, Agent, or Firm—Hopgood, Calimafde, Kalil, Blaustein & Judlowe

[57] ABSTRACT

A non-invasive method and an apparatus for detecting drug ingestion based upon the effects of drugs on corneo-retinal potential and/or brainwaves. The method comprises the steps of (a) determining a plurality of reference waveforms, each including corneo-retinal potential (CRP) and/or brainwave waveforms corresponding respectively to a plurality of drugs, (b) recording a subject's waveform while the subject is subjected to a static positional test, and (c) comparing the subject's measured waveforms with the reference waveforms to determine which drug or combination of drugs was ingested by the subject. The apparatus includes an improved electronystagmograph (ENG) machine modified to include longer leads and increased gain (amplification) than typically used for conventional applications.

11 Claims, 4 Drawing Figures

DRUG ABUSE DETECTION

RELATED APPLICATION

This is a continuation of U.S. application Ser. No. 297,997 filed on Aug. 31, 1981 which has been abandoned.

BACKGROUND OF THE INVENTION

Nystagmus is involuntary movement of the eyes. The nystagmus of human subjects will vary with certain disorders, principally disorders of the inner ear. It is known that the eye acts as an electrical dipole, with the cornea positive and the retina negative. The electric axis of the dipole is thus coincident with the optical axis of the eye. Electrodes placed on the skin adjacent the eyes will pick up voltages from the electric dipole, and these voltages will vary as does the eye movement. For example, electrodes of the temples will pick up voltages caused by horizontal eye movement which can be amplified and recorded to form a record of eye movement, both voluntary and involuntary. Instruments designed to pick up and record such voltages are known as electronystagmograph (ENG) machines. ENG machines have found extensive use in the prior art as an aid in diagnosing various ailments associated with the inner ear, for example, vertigo, Meniere's disease, lesions of the labyrinth and neurological ailments such as multiple sclerosis. In diagnosing vertigo, or in verifying a complaint of vertigo in compensation cases, the nystagmus of the subject is measured during positional or static tests in which the subject is placed in various positions. If vertigo is produced in any position its latency and fatigability is measured by repeated tests in this position. Active tests include spinning the subject in the two directions while seated in a rotatable chair with abrupt stops. This will produce vertigo of a few seconds duration in a normal subject, but longer periods indicated by the nystagmus recorded on the ENG for subjects with vertigo. Stimulatory or caloric tests involve irrigating the ear with 2½ cc of cold water. The water is removed after 20 seconds and the subject placed on his back with his head elevated 30° from the horizontal. The eye movement caused by the effect of the chilling of the fluids within the vestibular system is recorded on the ENG and compared to the normal duration of such eye movement to indicate disorders of this system.

ENG machines have also been used to measure the effect of anti-motion sickness remedies which suppress the normal function of the vestibular system in maintaining balance.

It has been known that drugs can in a general manner affect the nystagmus and hence workers in this field have usually taken their patients off medication before making tests involving nystagmus, such as those described above.

The present invention on the other hand, takes advantage of the effect of drugs, especially dangerous narcotic drugs, on the waveform to provide a non-invasive technique for diagnosing ingestion of such drugs.

The method of recording nystagmus by measuring the electrical field around the eye was first presented by Schott in 1922 and again by Meyers in 1929. Although Meyers thought that it was actually measuring the action potentials of the extraocular muscles, it was later discovered that the corneo-retinal potential difference detected at the lateral orbital areas are proportional to the angle of movement of the eyes.

The ENG has been used since that time to aid in the diagnosis and treatment of the cause of vertigo and other ailments, as explained above.

The problems of driving while under the influence of drugs and/or alcohol are well documented in the literature. Studies have shown that 10 to 35% of serious injury accidents involve persons whose blood alcohol concentration (BAC) is 100 mg/100 ml or higher. It has been estimated that from 40 to 50% of all fatally injured drivers have had blood alcohol concentrations that exceed the legal limit. Another study has shown that a large percentage of drivers arrested for intoxication in Dallas County over a two year period were under the influence of drugs such as diazepam, methaqualone, and barbiturates in addition to alcohol. These findings have pointed up the necessity for developing an objective, practical method of ascertaining the quality and quantity of drugs in drivers accused of being "under the influence". The controversial results of subjective clinical examination and blood alcohol tests reported by Rasch in a 1969 issue of the Journal *Blutalkohol*, 28:11–21, have encouraged many investigators to attempt to set up a model for ascertaining the degree of impairment related to alcohol intake using objective methods. Nystagmus tests have been found to be one of the most reliable objective methods for this purpose. Penttila's model is probably the best known, in which he devised an optimal model for determining degree of impairment using 494 subjects after testing over 100 models containing several different subtests. Using regression analysis, nystagmus tests were found to be most valuable. The final results yielded a value of 42% for nystagmus tests in the overall model for determining the effects of alcohol on the sensory motor system of an individual. The work of Penttila and his co-workers is reported in the *J. of Medicine, Science and Law*, vol. 16, pp. 95–103, and in *Blutalkohol*, 12:24–38, 1975.

Various qualitative studies have been performed using the ENG to demonstrate the effects of alcohol on the peripheral and central nervous systems. These effects have ranged from decrease in intraocular pressure and deterioration of tracking eye movement to changes in dynamic visual acuity, sinusoidal tracking, oculomotor tracking and peripheral gaze nystagmus.

Umeda and Sakata in 1978, in attempting to establish a pattern of alcohol affects, found that in normal subjects, alcohol affects the oculomotor system in the following order: caloric eye pattern tracking difficulties, positional alcohol nystagmus (PAN), eye tracking pattern difficulties, and finally alcohol gaze nystagmus abnormalities. Their research indicates that alcohol affects the cerebellum first, that visual suppression function is affected by alcohol, and that positional alcohol nystagmus (PAN) appears at a relatively early stage after the consumption of alcohol. It has been fairly well established that PAN I appears within 15 to 30 minutes in normal subjects with even a small amount of alcohol ingestion. See the following articles on this subject: Howells, *British Medical Journal*, 1:1405–1406, 1956; Fregly et al, *Quarterly Journal of Studies of Alcohol*, 28:11–21, 1967; Ey, *Bericht Der Deutschen Opthalmologischen Gesellschaft*, 65:349–353, 1964; Gottesberg, *Medizinische Welt*, 17:429–432, 1943; Loos et al, *Blutalkohol*, 16:321–329, 1979; Aschan et al, *Quarterly Journal of Studies of Alcohol*, 17:381–405, 1956. In that last mentioned article, Aschan and his co-workers report that PAN I has been measured at blood alcohol levels as low as 0.38 per mil. PAN I is the stage in which the person is initially affected by the alcohol. In this stage the nystagmus beats in the direction in which the head is positioned.

In studies which required the subjects to perform tasks to assess the degree of motor impairment, the degree of nystagmus appears to be a better indicator than blood alcohol levels. See the above-cited articles, of Howells, Fregly et al, Gottesberg, Loos et al, and Penttila et al, as well as Heifer in *Blutalkohol*, 13:66-75, 1976; and Rauscke, *Medizinische, Stuttgart*, 12:460-465, 1958. Howells found that in every case, an increase of reaction time was evidenced with the appearance of nystagmus, indicating a parallel impairment of the central nervous system. Fregly reports that in measuring degree of ataxia in persons who had imbibed alcohol, ataxic responses were in very close agreement with the intensity of PAN I. Maximum ataxia was observed sooner than maximum blood alcohol levels, and the ataxia improved during the time when blood alcohol remained high. Fregly et al report in the above-cited article that nystagmus most often begins about half an hour after the beginning of intoxication, while blood alcohol levels peak after one hour, thus indicating a lack of correlation between blood alcohol level and the time of maximum impairment. The close relationship between sensory motor impairment and the appearance of nystagmus can also be seen in the Loos et al study, in which peaks in post rotary fixation nystagmus occurred 8 minutes after imbibing alcohol, sensory motor impairment peaked in 19 minutes, and breath alcohol peaked in 40 minutes after the end of drinking.

Although the value of the ENG in determining degree of impairment related to alcohol intake is well known as evidenced by the articles discussed above, its use with other drug intake for qualitative diagnostic purposes has not yet been appreciated by the scientific community.

The effects of certain drugs on the quick component of vestibular nystagmus has been reported by several investigators, see for example, Anderson, et al, *Neurology*, 8:741, 1958; Bender et al, *Progress in Neurology and Psychiatry*, 10:201, 1955; Jatho, Z., *J. of Laryngology Rhinology and Otology*, 44:1, 1965; Jongkees et al, *Acta Physiologica Pharmacologica Neerlandica*, 9:240-275, 1960; McCabe, *Laryngoscope*, 75:1619, 1965; Nathanson et al, *Medical Clinics of North America*, 701, May, 1958; and Palve et al, *European Journal of Clinical Pharmacology* 13:345-350, 1978. The influence of drugs and their action in combination with alcohol has also been studied to some degree by researchers. See for example, Mattila et al, *Archives Internationales de Pharmacodynamie et de Therapie*, 234, 236-246, 1978; Bochenek et al, *Acta Medica Polona*, 15:117-126, 1974; Tomits, *Ful Orr Gegegyogyaszat*, 8:26-30, 1962; Goldberg, *Quarterly Journal of Studies of Alcohol*, Supp. 1, 37-56, 1961. However, there is no indication in the literature that any direct method for specific diagnostic purposes, such as the method of the present invention, has been used or suggested by workers in this field, or that the waveforms have been specifically identified.

The objective of the studies which lead to the present invention were to determine if specific ENG printouts of waveforms could be obtained for different drugs for purposes of drug identification and to qualitatively analyze the effects of relatively small amounts of alcohol on the vestibular system.

SUMMARY OF THE INVENTION

The diagnostic technique, process or method of the present invention comprises the steps of: placing the electrodes of an ENG machine on the face of the subject in the usual manner and location, adjusting the gain of the ENG machine to a value sufficient to obtain a recording of the subject's waveform including corneoretinal potential (CRP) and/or brainwave caused solely by drug ingestion, recording the nystagmus of the subject during a static positional test, then comparing the resulting waveform as recorded on the ENG with waveforms previously derived (by the inventor) and characteristic of ingestion of different drugs to thereby determine which, if any, of such drugs the subject has ingested. The static positional test can comprise measurements, with eyes open or closed, for a standardized set of at-rest conditions including gaze-right and gaze-left, while seated, as well as gaze-down for a supine position in which the head is inclined first to one and then to the other side.

The novel apparatus used in this invention comprises an ENG type machine with a gain corresponding to the above criteria, which is higher than has been used in the prior art for measuring the larger nystagmus characteristic of the relatively larger eye movement with which prior art workers in this field have been concerned.

Broadly stated, the invention involves the recognition that different drugs produce distinctive measurable waveforms in humans as well as certain non-humans and that by recording the waveform of a subject with apparatus capable of picking up and recording the small voltages produced by such drug-induced nystagmus and correlating them with previously identified drug induced waveforms, a reliable and non-invasive test for drug ingestion results. These waveforms are produced by a CRP and/or brainwave of the subject.

While the invention can be practiced using a conventional ENG machine or one with certain minor modifications, for example increased lead length and/or higher than normal gain, the inventor is not certain that the ENG waveforms disclosed herein resulting from drug and alcohol ingestion are due solely to eye movement or nystagmus. Some of the distinctive waveforms have been obtained from subjects whose eye muscles have been paralyzed by the administration of an anesthetic. The distinctive waveforms may be due to eye movement, fluctuations in the CRP caused by the drug or alcohol ingestion, or brain waves which reach the electrodes, or any combination of these three causes.

The present invention was motivated by a need for a rapid and accurate qualitative and quantitative evaluation of drug and alcohol intake, especially during emergency situations such as drug overdose and alcohol intoxication cases. The present inventor has used the ENG machine to develop a non-invasive technique for identification of drug and alcohol intake and to study the effects of these substances on the vestibular system. The results indicate that alcohol, diazepam (a tranquilizer), opiates, barbiturates, cocaine, marijuana and hallucinogenic drugs produce distinct waveforms on the ENG which can be qualitatively evaluated. Potential uses of this technique include identification of drugs involved in overdose situations, even though the subject may be unconscious, monitoring anesthesia during surgery, evaluating drug effects on newborn infants, checking racehorses for drugs before and after races, and determining whether or not persons to be tested on a polygraph are under the influence of drugs.

The primary aspect of the invention is the ability to directly measure the effects of different categories of drugs, each drug category producing its own specific waveform which is a result of drug effects upon the corneal-retinal potential and brainwaves. It should be specifically noted that these waveforms are obtained with the patient in a static position. The only stimulus producing the specific waveforms is the specific drug upon the corneal retinal/brainwave complex. Other testings previously have only noted the effect of the drugs on ordinary tests as opposed to measuring the effects of the drugs upon the human body (corneal retinal potential and brainwave) specifically.

The novel diagnostic technique of the present invention also measures the effect of the ingested substance on the body's nervous system and is thus a direct indication of the degree of impairment of such system by the substance. Measurement of blood alcohol levels, which has been used in the past to indicate ability or inability to drive safely, is unreliable in that the tolerance or reaction to alcohol or drugs varies with individuals, and thus different individuals can exhibit widely different nervous system impairment with the same blood alcohol levels.

DETAILED DESCRIPTION OF PREFERRED EMBODIMENTS

Figure 1:
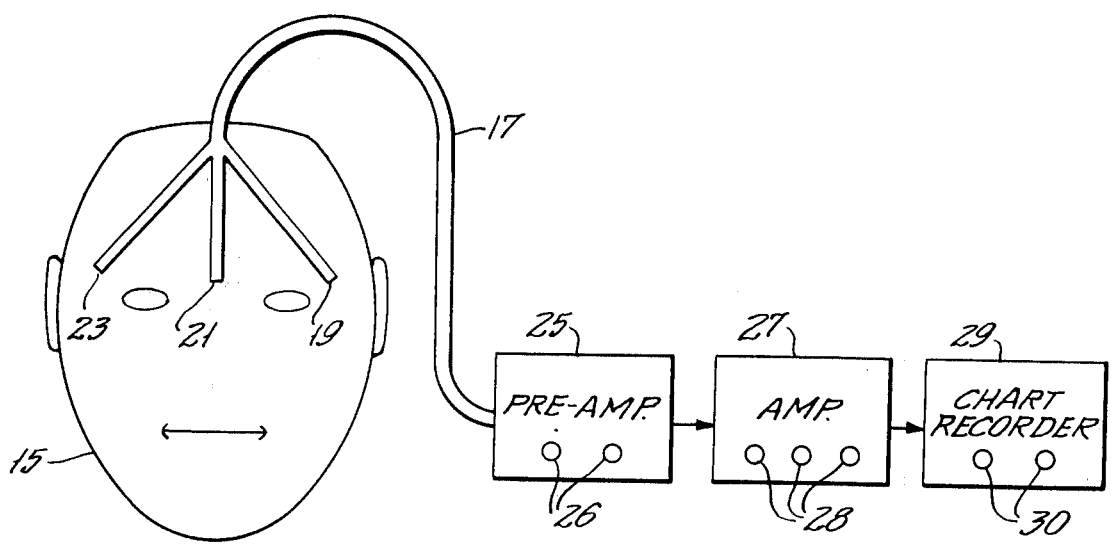
FIG. 1 is a schematic diagram of nystagmus-recording apparatus connected to practice the present invention.

A commercially available ENG machine was used, with three leads connected from the three facial electrodes to the ENG machine. One electrode was placed on the forehead between the eyes and the other two placed on the right and left temples. The test setup is illustrated in FIG. 1 in which the numerals 19, 21 and 23 represent the electrodes, all of which are connected to leads which are applied to the pre-amplifier 25 of the ENG machine via cable 17. The output of the pre-amplifier is applied to the amplifier 27 and thence to chart recorder 29. The ENG machine has controls indicated at 26, 28 and 30 to control to control gain, chart speed and other functions.

The test procedures were as follows: In the gaze tests the subject is instructed to fixate on an object 6 feet in front of him. He is then asked to look as far to the right as he can and hold this gaze for 20 seconds and then look back to center. This is repeated for a gaze to the left. For the positional alcohol nystagmus test (PAN), the subject is placed in a 30° supine position with the head to one side, and eyes looking down at the floor on that side, with both left and right sides tested.

Figure 2:
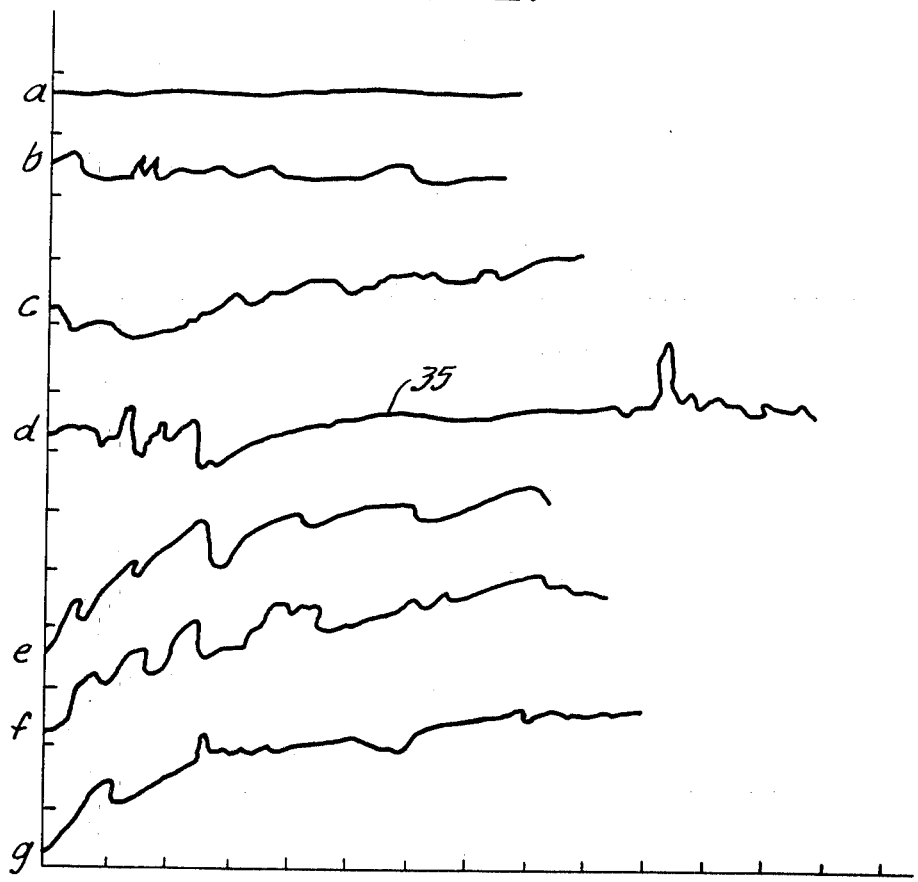
FIG. 2 is a succession of curves to show alcohol-induced nystagmus waveforms.

Subjects for the alcohol study fasted for 12 hours prior to testing. A baseline ENG was administered to all subjects, and all of the tests discussed above were administered. Curve a of FIG. 2 shows a typical baseline ENG for a typical subject. The ENG waveform at curve b of FIG. 2 is the ENG of the same subject taken 5 minutes after ingestion of 15 cc of 86.6 proof alcohol. Curve c of FIG. 2 is the ENG of the same person 15 minutes later, after taking an additional 15 cc of alcohol. Curve d of FIG. 2 is an eye open suppression test of the same subject. The subject's eyes were open during the central portion of this ENG printout, indicated by numeral 35, which portion is seen to be virtually flat, indicating little or no nystagmus. This indicates that the eyes are compensating for the vestibular impairment which causes the nystagmus with the eyes closed. This indicates that moderate doses of alcohol produce only peripheral effects. Curve e of FIG. 2 is a printout of another subject, 5 minutes after taking 5 cc of 86.6 proof alcohol; and curve f of FIG. 2 is the same person 15 minutes later after taking a second similar dosage. Curve g of FIG. 2 is the readout of the same person one hour later. All of the waveforms of FIG. 2 were made during PAN tests.

Nineteen persons were tested with diazepam or "Valium". Subjects were all on prescription for this drug and were instructed not to take any other drugs for 48 hours before testing. The dose was one 5 mg tablet twice a day and subjects reported for testing one hour after table ingestion. Subjects were tested at half hour intervals for 6 hours. All tests were administered to the diazepam subjects.

Sixteen subjects were tested with ketamine hydrochloride at hospitals while they were anesthetized. Tests of opiates included methadone hydrochloride and sublimase. All 5 of the methadone subjects were on maintenance programs and were given all of the tests described above. The 22 subjects tested with sublimase were all anesthetized in hospitals. Barbiturate tests were made with sodium pentathol in a hospital on 16 subjects while anesthetized. Ten subjects were administered cocaine in the nose during surgery while in the supine position, fixating, and eyes closed.

Results showed that small amounts of alcohol (15 cc) can affect the peripheral system after as little as 5 minutes. Twenty one subjects showed nystagmus 5 minutes after 15 cc of alcohol, and 34 subjects (63%) after the second 15 cc. Fifteen subjects showed nystagmus one hour after consuming 30 cc of alcohol.

Figure 3:
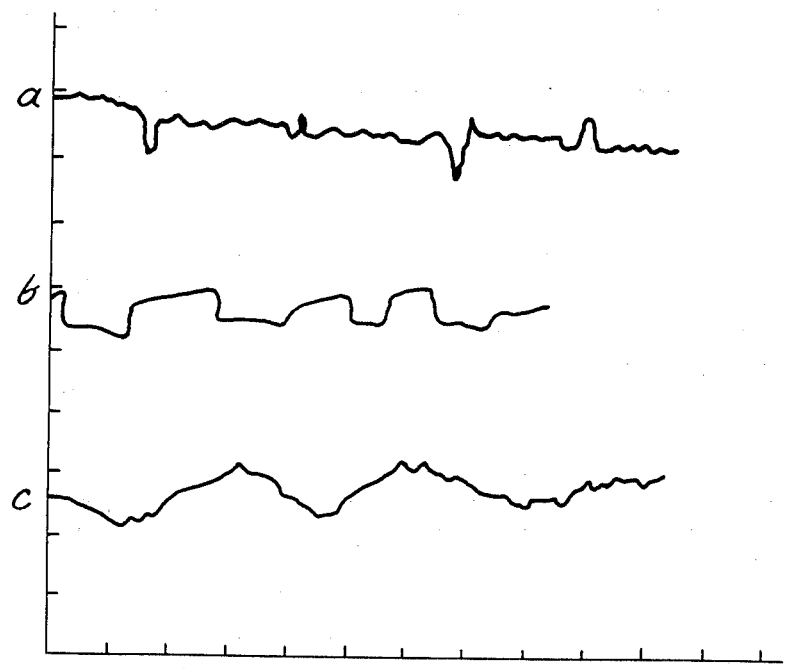
FIGS. 3 and 4 are separate succession of curves to show nystagmus waveforms induced by different drugs.
Figure 4:
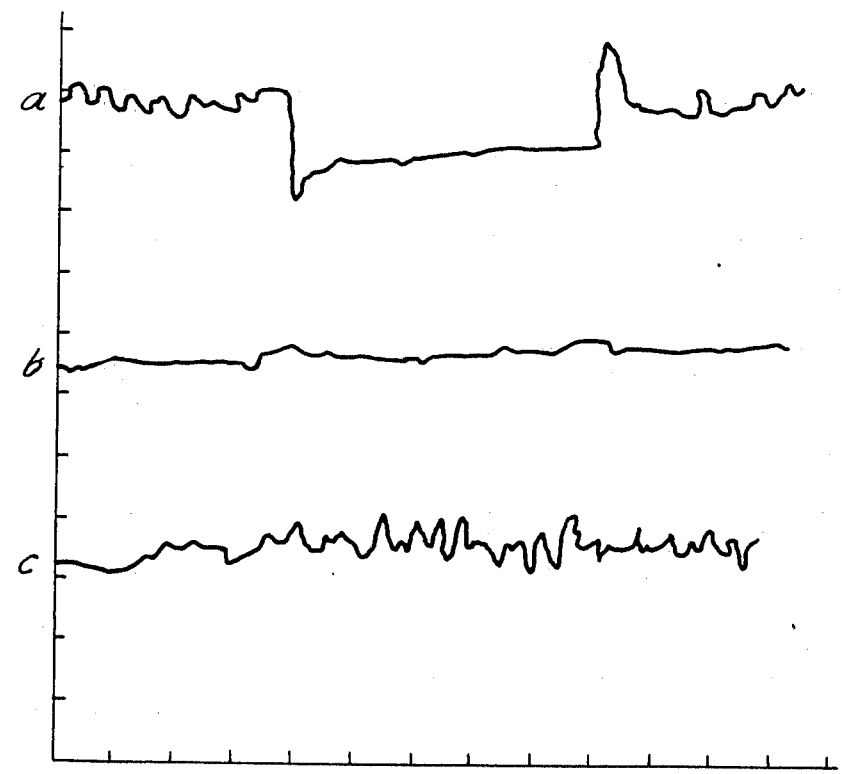

A sampling of the drug test ENG printouts is shown in FIGS. 3 and 4. The marks along the axes of FIGS. 2, 3 and 4 are spaced by 1 cm to establish the scale of the waveforms. Diazepam was found to have a depressor effect on the positional maintenance system and the vestibular end organ. Ketamine hydrochloride, which is chemically similar to PCP-Angel Dust, produced a pendular nystagmus which approached five to six hundred beats per minute with a lack of a slow or fast component, as seen in curve a of FIG. 3.

Sublimase methadone hydrochloride produced a "wandering" effect with squared waves, as seen in curve b of FIG. 3. Frequency and amplitude varied from subject to subject, but the squared wave was noted for all subjects.

As seen in the ENG printout of curve c of FIG. 3, sodium pentathol produced two or three hundred beats per minute, with an irregular amplitude ranging from 1 to 6 mm. The overall pattern resulted in a regular wandering effect, ranging between 7 and 9 seconds and 25 to 30 mm excursions.

Preliminary observations with marijuana show a peripheral effect when the subject is in the sitting position for calibration. Eye open suppression was complete, as indicated by the flat central portion of the marijuana waveform in curve a of FIG. 4 when the subject's eyes were open. The same position with eyes closed resulted in nystagmus specific to marijuana. Marijuana has a latent period and also a degree of fatigability compatible with peripheral effects.

The cocaine test described above produced a ripple effect as seen in curve b of FIG. 4 with waves of amplitude of one millimeter or less with an irregular frequency. The pattern was the same with eyes opened or closed.

The results of these drug studies reveal that certain drugs can be successfully identified by assessment of the frequency, amplitude and character of the ENG printout. All subjects produced a pattern which was specific to the drug administered. Research is continuing which indicates that combinations of drugs with other drugs and/or with alcohol results in a specific printout pattern also. An example of a dual drug waveform is that of curve c of FIG. 4, which results from ingestion of both diazepam and sodium pentathol. The reason for the distinctive ENG waveforms for different drugs is not known, however it may be a result of each drug affecting different parts of the brain, which influences the balancing mechanism.

The inventor is presently conducting a pilot study with certain state and local New Jersey law enforcement officials to ascertain the effectiveness of using this method to evaluate drug intake by individuals who are suspected of driving "under the influence". One of the subjects of this study is to determine whether or not the ENG machine can be used to provide quantitative information regarding drug intake.

In practicing this novel diagnostic method, electrodes are applied to the subject and connected to the ENG machine. The subject is then subjected to a static positional test.

The small drug-induced facial electrode voltages required to be picked up and recorded in the practice of this invention require ENG gains somewhat higher than has been used to record conventional nystagmus. At such high gains, care must be taken to avoid the picking up and recording of noise such as 60 cycle hum. The inventor has noted that by using longer than normal electrode leads, the noise performance of the ENG machine is improved despite the high gain setting used. The reason for this improved noise performance is not known. It is however advisable to use the minimum gain required and a recommended technique is to gradually increase the gain until a recognizable waveform appears, or it is obvious that none will appear.

As stated above, this technique has been tested and found effective on non-human subjects such as dogs and horses. It can be used to check racehorses and even racing dogs for drugs before or after races and provides an alternative to present drug tests which involve urinalysis. It is assumed that the present technique could be used on any species which exhibits a CRP/brainwave waveform, and this group is believed to include all mammals.

While the invention has been described in connection with what is presently considered to be the most practical and preferred embodiments, it is to be understood that the invention is not to be limited to the disclosed embodiments but on the contrary, is intended to cover various modifications and equivalent arrangements included within the spirit and scope of the appended claims which scope is to be accorded the broadest interpretation so as to encompass all such modifications and equivalent structures.

What is claimed is:

1. A non-invasive method of detecting drug ingestion by a subject comprising the steps of:
    (a) non-invasively establishing a plurality of reference waveforms by separately recording time-varying fluctuations in cornea-retinal potential (CRP) and/or brainwaves for each of a series of selected drugs administered to an individual who has been pre-examined for freedom from drugs, said recordings for each drug in the series being made in a standardized set of at-rest conditions;
    (b) non-invasively measuring the subject's waveform, by recording time-varying fluctuations in cornea-retinal potential (CPR) and/or brainwaves, for each of the at-rest conditions of said standardized set; and
    (c) comparing the subject's measured waveforms with said plurality of reference waveforms to ascertain the existence vel non of any correlation therebetween, thereby determining the presence or absence in said subject of any of said selected drugs.

2. A method according to claim 1 wherein both said recording step (a) and said measuring step (b) comprise the steps of:
    applying the electrodes of an ENG apparatus to the eye area of said individual and of said subject respectively; and
    amplifying the involved CRP signals.

3. A method according to claim 1 wherein a selected one of the drugs of step (a) is an opiate.

4. A method according to claim 1 wherein a selected one of the drugs of step (a) is a barbiturate.

5. A method according to claim 1 wherein a selected one of the drugs of step (a) is cocaine.

6. A method according to claim 1 wherein a selected one of the drugs of step (a) is diazepam, a tranquilizer.

7. A method according to claim 1 wherein a selected one of the drugs of step (a) is marijuana.

8. A method according to claim 1 wherein a selected one of the drugs of step (a) is ketamine hydrochloride, a hallucinogen.

9. The method of claim 1, in which said standardized set of at-rest conditions includes gaze-right and gaze-left, as well as gaze-down for a supine position in which the head is inclined to one and then to the other side.

10. The method of claim 9, in which the gaze-right and gaze-left conditions are for static positional seating, both for the individual of step (a) recordings and for the subject of step (b) measurements.

11. The method of claim 1, in which eyes are closed and opened for each of the recordings of step (a) and for the measurements of step (b).

* * * * *